United States Patent
Bitan et al.

(10) Patent No.: US 9,855,110 B2
(45) Date of Patent: Jan. 2, 2018

(54) METHODS, APPARATUS AND SYSTEMS FOR OPERATING A MEDICAL DEVICE INCLUDING AN ACCELEROMETER

(71) Applicant: Q-CORE MEDICAL LTD., Petach Tikva (IL)

(72) Inventors: Asher Bitan, Beit Hashmonai (IL); Arie Ramon, Herzeliya (IL); Shachar Rotem, Kibbutz Metzer (IL)

(73) Assignee: Q-CORE MEDICAL LTD., Netanya (IL)

( * ) Notice: Subject to any disclaimer, the term of this patent is extended or adjusted under 35 U.S.C. 154(b) by 976 days.

(21) Appl. No.: 13/759,181

(22) Filed: Feb. 5, 2013

(65) Prior Publication Data

US 2014/0222377 A1    Aug. 7, 2014

(51) Int. Cl.
*A61B 90/00*    (2016.01)
*G06F 19/00*    (2011.01)
*A61M 1/14*    (2006.01)

(52) U.S. Cl.
CPC .............. *A61B 90/36* (2016.02); *A61M 1/14* (2013.01); *G06F 19/3406* (2013.01); *A61M 2205/3561* (2013.01)

(58) Field of Classification Search
CPC ............. A61M 1/14; A61M 2205/3561; G06F 19/3406; A61B 19/52
USPC .................................. 702/183; 600/300, 485
See application file for complete search history.

(56) References Cited

U.S. PATENT DOCUMENTS

| | | |
|---|---|---|
| 2,056,322 A | 10/1936 | Hoppe |
| 2,393,838 A | 1/1946 | Tarbox |
| 2,743,898 A | 5/1956 | King |
| 2,981,115 A | 4/1961 | Beguin |
| 3,443,585 A | 5/1969 | Reinicke |
| 3,511,583 A | 5/1970 | Brown |
| 3,677,667 A | 7/1972 | Morrison |

(Continued)

FOREIGN PATENT DOCUMENTS

| | | |
|---|---|---|
| DE | 10118086 A1 | 7/2002 |
| EP | 0215249 A1 | 3/1987 |

(Continued)

OTHER PUBLICATIONS

Honeywell Sensing and Control, "FSSI500NSB force sensor", Golden Valley, Minnesota, USA, 1998-2004 http://sccatalog.honeywell.com/imc/printfriendly.asp?FAM~force&PN~FSSI500NSB (5 pages).

(Continued)

*Primary Examiner* — Manuel L Barbee
*Assistant Examiner* — Raymond Nimox
(74) *Attorney, Agent, or Firm* — Vladimir Sherman; Professional Patent Solutions

(57) ABSTRACT

Disclosed is a medical device, including: a therapeutic component adapted to provide therapeutic functionality while in therapeutic mode and further adapted to enter a device sleep mode (DSM), an accelerometer configured to identify a movement characterization of the therapeutic component and a movement analysis module (MAM) configured to receive the movement characterization from the accelerometer and determine a malfunction parameter wherein the MAM is operable while the therapeutic component is in the DSM.

15 Claims, 4 Drawing Sheets

(56) References Cited

U.S. PATENT DOCUMENTS

| | | | |
|---|---|---|---|
| 3,778,195 | A | 12/1973 | Bamberg |
| 3,982,722 | A | 9/1976 | Bernard |
| 3,982,725 | A | 9/1976 | Clark |
| 4,014,318 | A | 3/1977 | Dockum et al. |
| 4,039,269 | A | 8/1977 | Pickering |
| 4,155,362 | A | 5/1979 | Jess |
| 4,178,138 | A | 12/1979 | Iles |
| 4,236,880 | A | 12/1980 | Archibald |
| 4,270,532 | A | 6/1981 | Franetzki et al. |
| 4,290,346 | A | 9/1981 | Bujan |
| 4,320,781 | A | 3/1982 | Bouvet et al. |
| 4,373,525 | A | 2/1983 | Kobayashi |
| 4,450,375 | A | 5/1984 | Siegal |
| 4,479,797 | A | 10/1984 | Kobayashi et al. |
| 4,489,863 | A | 12/1984 | Horchos et al. |
| 4,493,706 | A | 1/1985 | Borsanyi et al. |
| 4,650,469 | A | 3/1987 | Berg et al. |
| 4,671,792 | A | 6/1987 | Borsanyi |
| 4,682,135 | A | 7/1987 | Yamakawa |
| 4,690,673 | A | 9/1987 | Bloomquist |
| 4,725,205 | A | 2/1988 | Cannon et al. |
| 4,728,265 | A | 3/1988 | Cannon |
| 4,741,736 | A | 5/1988 | Brown |
| 4,748,003 | A | 5/1988 | Riley |
| 4,755,168 | A | 7/1988 | Romanelli et al. |
| 4,836,752 | A | 6/1989 | Burkett |
| 4,867,744 | A | 9/1989 | Borsanyi |
| 4,893,991 | A | 1/1990 | Heminway et al. |
| 4,927,411 | A | 5/1990 | Pastrone et al. |
| 4,954,046 | A | 9/1990 | Irvin et al. |
| 4,954,256 | A | 9/1990 | Degen et al. |
| 4,978,335 | A | 12/1990 | Arthur, III |
| 5,074,756 | A | 12/1991 | Davis |
| 5,078,683 | A | 1/1992 | Sancoff et al. |
| 5,088,904 | A | 2/1992 | Okada |
| 5,096,385 | A | 3/1992 | Georgi et al. |
| 5,103,211 | A | 4/1992 | Daoud et al. |
| 5,151,019 | A | 9/1992 | Danby et al. |
| 5,152,680 | A | 10/1992 | Okada |
| 5,165,874 | A | 11/1992 | Sancoff et al. |
| 5,213,483 | A | 5/1993 | Flaherty et al. |
| 5,219,327 | A | 6/1993 | Okada |
| 5,222,946 | A | 6/1993 | Kamen |
| 5,246,347 | A | 9/1993 | Davis |
| 5,257,978 | A | 11/1993 | Haber et al. |
| 5,286,176 | A | 2/1994 | Bonin |
| 5,290,158 | A | 3/1994 | Okada |
| 5,308,333 | A | 5/1994 | Skakoon |
| 5,338,157 | A | 8/1994 | Blomquist |
| 5,395,320 | A | 3/1995 | Padda et al. |
| 5,429,485 | A | 7/1995 | Dodge |
| 5,485,408 | A | 1/1996 | Blomquist |
| 5,499,969 | A | 3/1996 | Beuchat et al. |
| 5,509,439 | A | 4/1996 | Tantardini |
| 5,527,295 | A | 6/1996 | Wing |
| 5,542,826 | A | 8/1996 | Warner |
| 5,569,188 | A | 10/1996 | Mackool |
| 5,575,309 | A | 11/1996 | Connell |
| 5,575,631 | A | 11/1996 | Jester |
| 5,577,891 | A | 11/1996 | Loughnane et al. |
| 5,584,667 | A | 12/1996 | Davis |
| 5,593,134 | A | 1/1997 | Steber et al. |
| 5,601,420 | A | 2/1997 | Warner et al. |
| 5,628,619 | A | 5/1997 | Wilson |
| 5,658,250 | A | 8/1997 | Blomquist et al. |
| 5,658,252 | A | 8/1997 | Johnson |
| 5,660,529 | A | 8/1997 | Hill |
| 5,669,877 | A | 9/1997 | Blomquist |
| 5,683,233 | A | 11/1997 | Moubayed et al. |
| 5,695,473 | A | 12/1997 | Olsen |
| 5,704,584 | A | 1/1998 | Winterer et al. |
| 5,742,519 | A | 4/1998 | McClendon et al. |
| 5,782,805 | A | 7/1998 | Meinzer et al. |
| 5,788,669 | A | 8/1998 | Peterson |
| 5,791,880 | A | 8/1998 | Wilson |
| 5,791,881 | A | 8/1998 | Moubayed et al. |
| 5,803,712 | A | 9/1998 | Davis et al. |
| 5,807,322 | A | 9/1998 | Lindsey et al. |
| 5,810,323 | A | 9/1998 | Winterer et al. |
| 5,853,386 | A | 12/1998 | Davis et al. |
| 5,876,370 | A | 3/1999 | Blomquist |
| 5,888,052 | A | 3/1999 | Hill |
| 5,896,076 | A | 4/1999 | Van Namen |
| 5,909,724 | A | 6/1999 | Nishimura et al. |
| 5,924,852 | A | 7/1999 | Moubayed et al. |
| 5,935,099 | A | 8/1999 | Peterson et al. |
| 5,935,106 | A | 8/1999 | Olsen |
| 5,943,633 | A | 8/1999 | Wilson et al. |
| 5,954,485 | A | 9/1999 | Johnson et al. |
| 5,980,490 | A | 11/1999 | Tsoukalis |
| 5,996,964 | A | 12/1999 | Ben-Shalom |
| 6,024,539 | A | 2/2000 | Blomquist |
| 6,095,189 | A | 8/2000 | Ben-Shalom |
| 6,110,153 | A | 8/2000 | Davis et al. |
| 6,146,109 | A | 11/2000 | Davis et al. |
| 6,164,921 | A | 12/2000 | Moubayed et al. |
| 6,165,874 | A | 12/2000 | Powell et al. |
| 6,168,569 | B1 * | 1/2001 | McEwen .................. A61B 5/16 600/557 |
| RE37,074 | E | 2/2001 | Danby et al. |
| 6,203,296 | B1 | 3/2001 | Ray et al. |
| 6,213,723 | B1 | 4/2001 | Danby et al. |
| 6,213,739 | B1 | 4/2001 | Phallen et al. |
| 6,234,773 | B1 | 5/2001 | Hill et al. |
| 6,241,704 | B1 | 6/2001 | Peterson et al. |
| 6,261,262 | B1 | 7/2001 | Briggs et al. |
| 6,280,408 | B1 | 8/2001 | Sipin |
| 6,312,227 | B1 | 11/2001 | Davis |
| 6,339,410 | B1 | 1/2002 | Milner et al. |
| 6,347,553 | B1 | 2/2002 | Morris et al. |
| 6,371,732 | B1 | 4/2002 | Moubayed et al. |
| 6,422,057 | B1 | 7/2002 | Anderson |
| 6,450,773 | B1 | 9/2002 | Upton |
| 6,475,180 | B2 | 11/2002 | Peterson et al. |
| 6,519,569 | B1 | 2/2003 | White et al. |
| 6,537,244 | B2 | 3/2003 | Paukovits et al. |
| 6,544,171 | B2 | 4/2003 | Beetz et al. |
| 6,558,347 | B1 | 5/2003 | Jhuboo et al. |
| 6,572,604 | B1 | 6/2003 | Platt et al. |
| 6,622,542 | B2 | 9/2003 | Derek et al. |
| 6,648,861 | B2 | 11/2003 | Platt et al. |
| 6,692,241 | B2 | 2/2004 | Watanabe et al. |
| 6,733,476 | B2 | 5/2004 | Christenson et al. |
| 6,742,992 | B2 | 6/2004 | Davis |
| 6,749,587 | B2 | 6/2004 | Flaherty |
| 6,768,425 | B2 | 7/2004 | Flaherty et al. |
| 6,788,199 | B2 | 9/2004 | Crabtree et al. |
| 6,790,198 | B1 | 9/2004 | White et al. |
| 6,902,549 | B2 | 6/2005 | Marmaropoulos et al. |
| 6,942,473 | B2 | 9/2005 | Abrahamson et al. |
| 7,018,361 | B2 | 3/2006 | Gillespie, Jr. et al. |
| 7,022,075 | B2 | 4/2006 | Grunwald et al. |
| 7,048,720 | B2 | 5/2006 | Thorne, Jr. et al. |
| 7,059,840 | B2 | 6/2006 | Corwin et al. |
| 7,122,026 | B2 | 10/2006 | Rogers et al. |
| 7,131,966 | B1 | 11/2006 | Tamari |
| 7,163,385 | B2 | 1/2007 | Gharib et al. |
| 7,347,836 | B2 | 3/2008 | Peterson et al. |
| 7,525,432 | B2 | 4/2009 | Jackson |
| 7,556,481 | B2 | 7/2009 | Moubayed |
| 7,645,258 | B2 | 1/2010 | White et al. |
| 7,654,976 | B2 | 2/2010 | Peterson et al. |
| 7,695,255 | B2 | 4/2010 | Ben-Shalom et al. |
| 7,698,156 | B2 | 4/2010 | Martucci et al. |
| 7,704,227 | B2 | 4/2010 | Moberg et al. |
| 7,762,795 | B2 | 7/2010 | Moubayed |
| 7,840,260 | B2 | 11/2010 | Epley |
| 7,848,811 | B2 * | 12/2010 | Moon .................. A61B 5/1116 607/19 |
| 7,892,332 | B2 | 2/2011 | Prisco et al. |
| 7,896,834 | B2 | 3/2011 | Smisson, III et al. |
| 7,935,102 | B2 | 5/2011 | Breznock et al. |
| 7,938,796 | B2 | 5/2011 | Moubayed et al. |
| 7,963,946 | B2 | 6/2011 | Moubayed et al. |

(56) References Cited

U.S. PATENT DOCUMENTS

| | | | |
|---|---|---|---|
| 7,998,121 B2 | 8/2011 | Stringham | |
| 8,025,634 B1 | 9/2011 | Moubayed et al. | |
| 8,029,253 B2 | 10/2011 | Rotem et al. | |
| 8,142,400 B2 | 3/2012 | Rotem et al. | |
| 8,182,445 B2 | 5/2012 | Moubayed et al. | |
| 8,197,235 B2 | 6/2012 | Davis | |
| 8,214,231 B2 | 7/2012 | Martucci et al. | |
| 8,234,128 B2 | 7/2012 | Martucci et al. | |
| 8,241,018 B2 | 8/2012 | Harr | |
| 8,257,654 B2 | 9/2012 | Maus et al. | |
| 8,308,457 B2 | 11/2012 | Rotem et al. | |
| 8,334,768 B2 | 12/2012 | Eaton et al. | |
| 8,337,168 B2 | 12/2012 | Rotem et al. | |
| 8,343,111 B2 | 1/2013 | Beck et al. | |
| 8,352,290 B2 | 1/2013 | Bartz et al. | |
| 8,363,583 B2 | 1/2013 | Jia et al. | |
| 8,371,832 B2 | 2/2013 | Rotem et al. | |
| 8,444,587 B2 | 5/2013 | Kelly et al. | |
| 8,489,427 B2 | 7/2013 | Simpson et al. | |
| 8,535,025 B2 | 9/2013 | Rotem et al. | |
| 8,545,436 B2* | 10/2013 | Robertson | A61B 5/0006 455/227 |
| 8,579,816 B2 | 11/2013 | Kamath et al. | |
| 8,666,367 B2 | 3/2014 | Sharp et al. | |
| 8,672,875 B2 | 3/2014 | Vanderveen et al. | |
| 8,678,793 B2 | 3/2014 | Goldor et al. | |
| 8,825,166 B2* | 9/2014 | John | A61N 2/02 607/45 |
| 8,920,144 B2 | 12/2014 | Rotem et al. | |
| 9,056,160 B2 | 6/2015 | Rotem et al. | |
| 2001/0029321 A1 | 10/2001 | Beetz et al. | |
| 2002/0056675 A1 | 5/2002 | Hegde | |
| 2002/0094287 A1 | 7/2002 | Davis | |
| 2002/0156402 A1 | 10/2002 | Woog et al. | |
| 2002/0165503 A1 | 11/2002 | Morris et al. | |
| 2003/0034887 A1 | 2/2003 | Crabtree et al. | |
| 2003/0040700 A1 | 2/2003 | Hickle et al. | |
| 2003/0065536 A1 | 4/2003 | Hansen et al. | |
| 2003/0109988 A1 | 6/2003 | Geissler et al. | |
| 2003/0140928 A1 | 7/2003 | Bui et al. | |
| 2003/0141981 A1 | 7/2003 | Bui et al. | |
| 2003/0182586 A1 | 9/2003 | Numano | |
| 2003/0212311 A1* | 11/2003 | Nova et al. | 600/300 |
| 2004/0049233 A1* | 3/2004 | Edwards | 607/5 |
| 2004/0167804 A1 | 8/2004 | Simpson et al. | |
| 2004/0172222 A1 | 9/2004 | Simpson et al. | |
| 2004/0181314 A1 | 9/2004 | Zaleski | |
| 2004/0191112 A1 | 9/2004 | Hill et al. | |
| 2004/0204673 A1 | 10/2004 | Flaherty | |
| 2004/0204685 A1 | 10/2004 | Wright et al. | |
| 2004/0235446 A1 | 11/2004 | Flaherty et al. | |
| 2005/0001369 A1 | 1/2005 | Cross | |
| 2005/0022274 A1 | 1/2005 | Campbell et al. | |
| 2005/0055242 A1 | 3/2005 | Bello et al. | |
| 2005/0076909 A1* | 4/2005 | Stahmann | A61B 5/0031 128/204.23 |
| 2005/0088409 A1 | 4/2005 | Van Berkel | |
| 2005/0112001 A1 | 5/2005 | Bahnen et al. | |
| 2005/0171501 A1 | 8/2005 | Kelly | |
| 2005/0191196 A1 | 9/2005 | Tanner et al. | |
| 2005/0214146 A1 | 9/2005 | Corwin et al. | |
| 2006/0051218 A1 | 3/2006 | Harttig | |
| 2006/0083644 A1 | 4/2006 | Zumbrum et al. | |
| 2006/0173419 A1 | 8/2006 | Malcolm | |
| 2006/0213249 A1 | 9/2006 | Uram et al. | |
| 2007/0032098 A1 | 2/2007 | Bowles et al. | |
| 2007/0048161 A1 | 3/2007 | Moubayed | |
| 2007/0060872 A1 | 3/2007 | Hall et al. | |
| 2007/0118405 A1 | 5/2007 | Campbell et al. | |
| 2007/0135866 A1 | 6/2007 | Baker et al. | |
| 2007/0154336 A1 | 7/2007 | Miyazaki et al. | |
| 2007/0167850 A1* | 7/2007 | Russell | A61B 5/0205 600/513 |
| 2007/0217931 A1 | 9/2007 | Estes et al. | |
| 2007/0269324 A1 | 11/2007 | Goldor et al. | |
| 2008/0015506 A1 | 1/2008 | Davis | |
| 2008/0065007 A1 | 3/2008 | Peterson et al. | |
| 2008/0065016 A1 | 3/2008 | Peterson et al. | |
| 2008/0067462 A1 | 3/2008 | Miller et al. | |
| 2008/0071251 A1 | 3/2008 | Moubayed et al. | |
| 2008/0081958 A1* | 4/2008 | Denison | A61N 1/3706 600/300 |
| 2008/0095649 A1 | 4/2008 | Ben-Shalom et al. | |
| 2008/0144560 A1 | 6/2008 | Jia et al. | |
| 2008/0145249 A1 | 6/2008 | Smisson et al. | |
| 2008/0146995 A1 | 6/2008 | Smisson et al. | |
| 2008/0275307 A1 | 11/2008 | Poschmann | |
| 2009/0088675 A1 | 4/2009 | Kelly et al. | |
| 2009/0163864 A1 | 6/2009 | Breznock et al. | |
| 2009/0203329 A1 | 8/2009 | White et al. | |
| 2009/0221964 A1 | 9/2009 | Rotem et al. | |
| 2009/0240201 A1 | 9/2009 | Rotem et al. | |
| 2009/0270810 A1 | 10/2009 | DeBelser et al. | |
| 2009/0300507 A1 | 12/2009 | Raghavan et al. | |
| 2009/0317268 A1 | 12/2009 | Rotem et al. | |
| 2010/0016781 A1 | 1/2010 | Nakayama et al. | |
| 2010/0036322 A1 | 2/2010 | Rotem | |
| 2010/0082001 A1 | 4/2010 | Beck et al. | |
| 2010/0168545 A1 | 7/2010 | Kamath et al. | |
| 2010/0211002 A1 | 8/2010 | Davis | |
| 2010/0228223 A1 | 9/2010 | Williams et al. | |
| 2010/0234708 A1 | 9/2010 | Buck et al. | |
| 2010/0279652 A1 | 11/2010 | Sharp et al. | |
| 2011/0054264 A1* | 3/2011 | Fischell | A61B 5/0031 600/300 |
| 2011/0054334 A1* | 3/2011 | Fischell | A61B 5/0402 600/509 |
| 2011/0098608 A1* | 4/2011 | Griffiths | A61B 5/1114 600/595 |
| 2011/0148624 A1 | 6/2011 | Eaton et al. | |
| 2011/0152772 A1 | 6/2011 | Rotem et al. | |
| 2011/0152831 A1 | 6/2011 | Rotem et al. | |
| 2011/0167133 A1 | 7/2011 | Jain | |
| 2011/0251856 A1 | 10/2011 | Maus et al. | |
| 2011/0264043 A1 | 10/2011 | Kotnik et al. | |
| 2011/0276000 A1 | 11/2011 | Stringham | |
| 2011/0282291 A1 | 11/2011 | Ciccone | |
| 2011/0318208 A1 | 12/2011 | Goldor et al. | |
| 2012/0059389 A1 | 3/2012 | Larson et al. | |
| 2012/0062387 A1 | 3/2012 | Vik et al. | |
| 2012/0101411 A1* | 4/2012 | Hausdorff | A61B 5/1117 600/595 |
| 2012/0136305 A1 | 5/2012 | Gagliardoni et al. | |
| 2012/0241525 A1 | 9/2012 | Borges et al. | |
| 2013/0006666 A1 | 1/2013 | Schneider et al. | |
| 2013/0046508 A1 | 2/2013 | Sur et al. | |
| 2013/0116620 A1 | 5/2013 | Rotem et al. | |
| 2013/0116623 A1 | 5/2013 | Rotem et al. | |
| 2013/0142670 A1 | 6/2013 | Rotem et al. | |
| 2013/0209275 A1 | 8/2013 | Rotem et al. | |
| 2013/0279370 A1 | 10/2013 | Eitan et al. | |
| 2013/0345623 A1 | 12/2013 | Kopperschmidt et al. | |
| 2014/0005631 A1 | 1/2014 | Rotem et al. | |
| 2014/0031635 A1* | 1/2014 | Sabesan | A61B 5/7282 600/301 |
| 2014/0119954 A1 | 5/2014 | Schweitzer et al. | |
| 2014/0197824 A1 | 7/2014 | Gillespie et al. | |
| 2014/0222377 A1 | 8/2014 | Bitan et al. | |
| 2014/0276564 A1 | 9/2014 | Schneider | |
| 2014/0369872 A1 | 12/2014 | Goldor et al. | |
| 2014/0378901 A1 | 12/2014 | Rotem et al. | |
| 2015/0038187 A1 | 2/2015 | Ho et al. | |
| 2015/0073338 A1 | 3/2015 | Waldhoff et al. | |
| 2015/0105726 A1 | 4/2015 | Qi et al. | |
| 2015/0137988 A1 | 5/2015 | Gravenstein et al. | |
| 2015/0141955 A1 | 5/2015 | Ruchti et al. | |
| 2015/0172921 A1 | 6/2015 | Wang et al. | |

(56) References Cited

U.S. PATENT DOCUMENTS

| | | |
|---|---|---|
| 2015/0182694 A1 | 7/2015 | Rosinko |
| 2015/0192120 A1 | 7/2015 | Rotem et al. |

FOREIGN PATENT DOCUMENTS

| | | |
|---|---|---|
| EP | 0225158 A2 | 6/1987 |
| EP | 0315312 A1 | 5/1989 |
| EP | 0429866 A1 | 6/1991 |
| EP | 0483794 A1 | 5/1992 |
| EP | 0858812 A2 | 8/1998 |
| EP | 1031358 A1 | 8/2000 |
| EP | 1350955 A2 | 10/2003 |
| EP | 1557186 | 7/2005 |
| EP | 1611834 A2 | 1/2006 |
| EP | 1485149 B1 | 7/2008 |
| FR | 2632529 A1 | 12/1989 |
| FR | 2753236 A1 | 3/1998 |
| JP | 60043188 A | 3/1985 |
| JP | 6-169992 A | 6/1994 |
| JP | 2002-57738 A | 2/2002 |
| JP | 2004141418 A | 5/2004 |
| WO | 8400691 A1 | 3/1984 |
| WO | 9116933 A1 | 11/1991 |
| WO | 9325816 A1 | 12/1993 |
| WO | 9408647 A1 | 4/1994 |
| WO | 9603168 A1 | 2/1996 |
| WO | 9630679 A1 | 10/1996 |
| WO | 9734084 A1 | 9/1997 |
| WO | 9804301 A1 | 2/1998 |
| WO | 9813080 A2 | 4/1998 |
| WO | 9847551 A1 | 10/1998 |
| WO | 99/58178 A1 | 11/1999 |
| WO | 0139816 A2 | 6/2001 |
| WO | 0165232 A1 | 9/2001 |
| WO | 0236044 A2 | 5/2002 |
| WO | 0238204 A2 | 5/2002 |
| WO | 0249509 A2 | 6/2002 |
| WO | 02068015 A2 | 9/2002 |
| WO | 03027503 A1 | 4/2003 |
| WO | 03080158 A1 | 10/2003 |
| WO | 2004070548 A2 | 8/2004 |
| WO | 2004093648 A2 | 11/2004 |
| WO | 2005089263 A2 | 9/2005 |
| WO | 2006/056986 A1 | 6/2006 |
| WO | 2007133259 A1 | 11/2007 |
| WO | 2008036658 A2 | 3/2008 |
| WO | 2008059492 A2 | 5/2008 |
| WO | 2008059493 A2 | 5/2008 |
| WO | 2008059494 A2 | 5/2008 |
| WO | 2008059495 A2 | 5/2008 |
| WO | 2008059496 A2 | 5/2008 |
| WO | 2008059498 A2 | 5/2008 |
| WO | 2008059499 A2 | 5/2008 |
| WO | 2008130644 A1 | 10/2008 |
| WO | 2010053702 A1 | 5/2010 |
| WO | 2010053703 A1 | 5/2010 |
| WO | 2010091313 A2 | 8/2010 |
| WO | 2011128850 A2 | 10/2011 |
| WO | 2012095827 A1 | 7/2012 |
| WO | 2012095829 A2 | 7/2012 |
| WO | 2013001425 A1 | 1/2013 |
| WO | 2013/028704 A1 | 2/2013 |
| WO | 2013/090748 A1 | 6/2013 |

OTHER PUBLICATIONS

International Application PCT/IL2007/001398 Search Report dated Jun. 11, 2008 (2 pages).
International Application PCT/IL2007/001398 Patentability Report dated May 19, 2009 (6 pages).
International Application PCT/IL2007/001399 Search Report dated Jun. 4, 2008 (3 pages).
International Application PCT/IL2007/001399 Patentability Report dated May 19, 2009 (9 pages).
International Application PCT/IL2007/001400 Search Report dated Jul. 15, 2008 (3 pages).
International Application PCT/IL2007/001400 Patentability Report dated May 19, 2009 (10 pages).
International Application PCT/IL2007/001401 Search Report dated Sep. 24, 2008 (2 pages).
International Application PCT/IL2007/001401 Patentability Report dated May 19, 2009 (11 pages).
International Application PCT/IL2007/001402 Search Report dated Jun. 20, 2008 (3 pages).
International Application PCT/IL2007/001402 Patentability Report dated May 19, 2009 (4 pages).
International Application PCT/IL2007/001404 Search Report dated Jul. 14, 2008 (2 pages).
International Application PCT/IL2007/001404 Patentability Report dated May 19, 2009 (7 pages).
International Application PCT/IL2007/001405 Search Report dated Jul. 21, 2008 (4 pages).
International Application PCT/IL2007/001405 Patentability Report dated May 19, 2009 (7 pages).
International Application PCT/IL2005/001249 Search Report dated Apr. 5, 2006 (18 pages).
International Application PCT/IL1997/000289 Search report dated Jan. 27, 1998 (18 pages).
International Application PCT/IL1997/000290 Search Report dated Jan. 27, 1998 (18 pages).
International Application PCT/IL2003/000947 Search Report dated Mar. 3, 2004 (43 pages).
International Application PCT/IB2011/051586 Search Report dated Oct. 27, 2011 (3 pages).
International Application PCT/IB2011/051586 Patentability Report dated Oct. 16, 2012 (9 pages).
International Application PCT/IB2012/050192 Search Report dated Aug. 17, 2012 (2 pages).
International Application PCT/IB2012/050192 Patentability Report dated Jul. 16, 2013 (6 pages).
International Application PCT/IB2012/050189 Search Report dated May 30, 2012 (2 pages).
International Application PCT/IB2012/050189 Patentability Report dated Jul. 16, 2013 (5 pages).
International Application PCT/IB2012/053149 Search Report dated Jan. 15, 2013 (2 pages).
U.S. Appl. No. 09/125,438 Official Action dated May 3, 1999 (4 pages).
U.S. Appl. No. 09/125,438 Official Action dated Jul. 15, 1999 (7 pages).
U.S. Appl. No. 10/535,103 Official Action dated Feb. 2, 2009 (9 pages).
European Application No. 05810500.8 Official Action dated Jul. 6, 2009 (5 pages).
European Application No. 05810500.8 Response to Official Action dated Jul. 6, 2009, submitted Oct. 15, 2009 (8 pages).
European Application No. 05810500.8 Official Action dated Jan. 23, 2012 (4 pages).
European Application No. 05810500.8 Response to Official Action dated Jan. 23, 2012, submitted May 22, 2012 (6 pages).
U.S. Appl. No. 11/791,599 Official Action (Non-Final) dated Aug. 19, 2010 (16 pages).
U.S. Appl. No. 11/791,599 Response to Official Action (Non-Final) dated Aug. 19, 2010, submitted Jan. 11, 2011 (8 pages).
U.S. Appl. No. 11/791,599 Official Action (Final) dated Mar. 31, 2011 (13 pages).
U.S. Appl. No. 11/791,599 Response to Official Action (Final) dated Mar. 31, 2011, submitted May 23, 2011 (7 pages).
U.S. Appl. No. 11/791,599 Notice of Allowance dated Jun. 14, 2011 (5 pages).
U.S. Appl. No. 13/229,798 Official Action (Non-Final) dated Dec. 26, 2012 (10 pages).
U.S. Appl. No. 13/229,798 Response to Official Action (Non-Final) dated Dec. 26, 2012, submitted Mar. 21, 2013 (13 pages).
U.S. Appl. No. 13/229,798 Notice of Allowance dated Apr. 19, 2013 (6 pages).

(56) References Cited

OTHER PUBLICATIONS

U.S. Appl. No. 13/229,798 Notice of Withdrawal from Issue dated May 13, 2013 (1 page).
U.S. Appl. No. 13/229,798 Official Action (Non-Final) dated Jun. 21, 2013 (6 pages).
Chinese Patent Application No. 200580045471.3 "Finger-type peristaltic pump" Official Action dated Jul. 18, 2008 and English translation thereof (7 pages).
Chinese Patent Application No. 200780041966.8 Official Action dated Jul. 13, 2010 (7 pages).
Chinese Patent Application No. 200780041966.8 Response to Official Action dated Jul. 13, 2010, as submitted (6 pages).
Chinese Patent Application No. 200780041966.8, translation of Notification of Grant, dated Jan. 28, 2011 (2 pages).
U.S. Appl. No. 12/464,202 Official Action (Non-Final) dated Oct. 3, 2011 (7 pages).
U.S. Appl. No. 12/464,202 Response to Official Action (Non-Final) dated Oct. 3, 2011, submitted Feb. 12, 2012 (12 pages).
U.S. Appl. No. 12/464,202 Notice of Allowance dated Jul. 11, 2012 (5 pages).
U.S. Appl. No. 12/463,399 Official Action (Non-Final) dated Jul. 21, 2011 (15 pages).
U.S. Appl. No. 12/463,399 Response to Official Action (Non-Final) dated Jul. 21, 2011, submitted Oct. 21, 2011 (5 pages).
U.S. Appl. No. 12/463,399 Official Action (Final) dated Dec. 13, 2011 (7 pages).
U.S. Appl. No. 12/463,399 Response to Official Action (Final) dated Dec. 13, 2011, submitted Feb. 12, 2012 (10 pages).
U.S. Appl. No. 12/463,399 Advisory Action and Applicant Initiated Interview Summary dated Mar. 8, 2012 (8 pages).
U.S. Appl. No. 12/463,399 Response to Official Action (Final) dated Dec. 13, 2011, submitted Mar. 26, 2012 with Request for Continued Examination (13 pages).
U.S. Appl. No. 12/463,399 Notice of Allowance dated Apr. 29, 2013 (14 pages).
U.S. Appl. No. 12/514,310 Official Action (Non-Final) dated Jul. 21, 2011 (8 pages).
U.S. Appl. No. 12/514,310 Response to Official Action (Non-Final) dated Jul. 21, 2011, submitted Oct. 21, 2011 (8 pages).
U.S. Appl. No. 12/514,310 Official Action (Final) dated Jan. 20, 2012 (10 pages).
U.S. Appl. No. 12/514,310 Response to Official Action (Final) dated Jan. 20, 2012, submitted Apr. 25, 2012 with Request for Continued Examination (11 pages).
U.S. Appl. No. 12/514,310 Official Action (Non-Final) dated May 25, 2012 (7 pages).
U.S. Appl. No. 12/514,310 Response to Official Action (Non-Final) dated May 25, 2012, submitted Jun. 28, 2012 (6 pages).
U.S. Appl. No. 12/514,310 Notice of Allowance dated Aug. 22, 2012 (7 pages).
U.S. Appl. No. 12/514,311 Official Action (Non-Final) dated Sep. 16, 2010 (10 pages).
U.S. Appl. No. 12/514,311 Response to Official Action (Non-Final) dated Sep. 16, 2010, submitted Dec. 9, 2010 (23 pages).
U.S. Appl. No. 12/514,311 Official Action (Final) dated Feb. 18, 2011, (7 pages).
U.S. Appl. No. 12/514,311 Examiner Interview Summary Record dated Mar. 4, 2011 (4 pages).
U.S. Appl. No. 12/514,311 Response to Official Action (Final) dated Feb. 18, 2011, submitted Mar. 31, 2011 with Request for Continued Examination (9 pages).
European Patent Application No. 10192477.7 Search Report dated May 10, 2011 (5 pages).
European Patent Application No. 10192477.7 Response to Search Report dated May 10, 2011, submitted Dec. 28, 2011.
U.S. Appl. No. 12/644,026 Official Action (Non-Final) dated Apr. 6, 2012 (12 pages).
U.S. Appl. No. 12/644,026 Response to Official Action (Non-Final) dated Apr. 6, 2012, submitted Jul. 5, 2012 (11 pages).
U.S. Appl. No. 12/644,026 Notice of Allowance dated Oct. 11, 2012 (10 pages).
U.S. Appl. No. 13/742,454 Official Action (Non-Final) dated Oct. 7, 2013 (13 pages).
U.S. Appl. No. 12/644,027 Official Action (Non-Final) dated Apr. 28, 2011 (7 pages).
U.S. Appl. No. 12/644,027 Response to Official Action (Non-Final) dated Apr. 28, 2011, submitted Jul. 21, 2011 (10 pages).
U.S. Appl. No. 12/644,027 Notice of Allowance dated Nov. 17, 2011 (5 pages).
U.S. Appl. No. 13/229,798 Response to Official Action (Non-Final) dated Jun. 21, 2013, submitted Oct. 21, 2013 (3 pages).
U.S. Appl. No. 13/229,798 Notice of Allowance dated Nov. 14, 2013 (54 pages).
U.S. Appl. No. 13/651,420 Official Action (Non-Final) dated Nov. 4, 2013 (8 pages).
U.S. Appl. No. 13/651,420 Response to Official Action (Non-Final) dated Nov. 4, 2013, submitted Nov. 21, 2013 (2 pages).
U.S. Appl. No. 13/681,440 Official Action (Non-Final) dated Oct. 24, 2013 (11 pages).
U.S. Appl. No. 13/651,420 Official Action (Non-Final) dated Jan. 6, 2014 (8 pages).
U.S. Appl. No. 13/651,420 Response to Official Action (Non-Final) dated Jan. 6, 2014, submitted Mar. 5, 2014 (9 pages).
U.S. Appl. No. 13/651,420 Official Action (Final) dated Apr. 24, 2014 (8 pages).
U.S. Appl. No. 13/651,420 Response to Official Action (Final) dated Apr. 24, 2014, submitted Jul. 22, 2014 with Request for Continued Examination (15 pages).
U.S. Appl. No. 13/651,420 Official Action (Non-Final) dated Aug. 19, 2014 (10 pages).
U.S. Appl. No. 13/651,420 Response to Official Action (Non-Final) dated Aug. 19, 2014, submitted Dec. 18, 2014 (7 pages).
U.S. Appl. No. 14/016,105 Official Action (Non-Final) dated Oct. 15, 2014 (10 pages).
U.S. Appl. No. 13/681,440 Response to Official Action (Non-Final) dated Oct. 24, 2013, submitted Jan. 20, 2014 (10 pages).
U.S. Appl. No. 13/681,440 Official Action (Final) dated Feb. 14, 2014 (14 pages).
U.S. Appl. No. 13/681,440 Response to Official Action (Final) dated Feb. 14, 2014, submitted Jul. 14, 2014 with Request for Continued Examination (14 pages).
U.S. Appl. No. 13/681,440 Official Action (Non-Final) dated Sep. 2, 2014 (19 pages).
U.S. Appl. No. 12/514,311 Official Action (Non-Final) dated Oct. 7, 2014 (11 pages).
U.S. Appl. No. 13/742,454 Response to Official Action (Non-Final) dated Oct. 7, 2013, submitted Jan. 6, 2014 (7 pages).
U.S. Appl. No. 13/742,454 Official Action (Final) dated Mar. 28, 2014 (14 pages).
U.S. Appl. No. 13/742,454 Response to Official Action (Final) dated Mar. 28, 2014, submitted Jun. 29, 2014 with Request for Continued Examination (10 pages).
U.S. Appl. No. 13/742,454 Notice of Allowance dated Aug. 21, 2014 (10 pages).
U.S. Appl. No. 13/640,519 Official Action (Non-Final) dated Dec. 24, 2013 (7 pages).
U.S. Appl. No. 13/640,519 Response to Official Action (Non-Final) dated Dec. 24, 2013, submitted Jan. 16, 2014 (2 pages).
U.S. Appl. No. 13/640,519 Official Action (Non-Final) dated Mar. 20, 2014 (15 pages).
U.S. Appl. No. 13/640,519 Response to Official Action (Non-Final) dated Mar. 20, 2014, submitted Jun. 17, 2014 (14 pages).
U.S. Appl. No. 13/640,519 Official Action (Final) dated Oct. 1, 2014 (11 pages).
U.S. Appl. No. 13/924,572 Official Action (Non-Final) dated Dec. 2, 2014 (13 pages).
European Application No. 11768544.6 Supplementary Partial European Search Report dated Nov. 13, 2014 (7 pages).
European Application No. 12734200.4 Supplementary European Search Report dated Aug. 18, 2014 (6 pages).
European Application No. 05810500.8 Official Action dated Nov. 3, 2014 (5 pages).

(56) References Cited

OTHER PUBLICATIONS

European Application No. 05810500.8 Response to Official Action dated Nov. 3, 2014, submitted Mar. 9, 2015 (31 pages).
Indian Patent Application No. 2344KOLNP2007 Office Action dated Dec. 31, 2014 (2 pages).
Indian Patent Application No. 2344KOLNP2007 Response to Office Action dated Dec. 31, 2014, submitted Aug. 7, 2015 (19 pages).
U.S. Appl. No. 14/181,673 Official Action (Non-Final) dated Jun. 3, 2015 (12 pages).
U.S. Appl. No. 13/651,420 Official Action (Final) dated Mar. 16, 2015 (6 pages).
U.S. Appl. No. 13/651,420 Response to Official Action (Final) dated Mar. 16, 2015, submitted May 14, 2015 (5 pages).
U.S. Appl. No. 13/651,420 Official Action (Final) dated Jun. 9, 2015 (9 pages).
U.S. Appl. No. 14/016,105 Response to Official Action (Non-Final) dated Oct. 15, 2014, submitted Jan. 14, 2015 (7 pages).
U.S. Appl. No. 14/016,105 Notice of Allowance dated Feb. 17, 2015 (14 pages).
U.S. Appl. No. 13/681,440 Response to Official Action (Non-Final) dated Sep. 2, 2014, submitted Feb. 25, 2015 (12 pages).
U.S. Appl. No. 13/681,440 Official Action (Final) dated Apr. 24, 2015 (21 pages).
U.S. Appl. No. 12/514,311 Response to Official Action (Non-Final) dated Oct. 7, 2014, submitted Jan. 7, 2015 (5 pages).
U.S. Appl. No. 12/514,311 Official Action (Final) dated Apr. 20, 2015 (12 pages).
U.S. Appl. No. 12/514,311 Response to Official Action (Final) dated Apr. 20, 2015, submitted Jun. 21, 2015 (10 pages).
U.S. Appl. No. 12/514,311 Official Action (Advisory Action) dated Jul. 1, 2015 (8 pages).
U.S. Appl. No. 12/514,311 Response to Official Action (Advisory Action) dated Jul. 1, 2015, submitted Jul. 20, 2015 (8 pages).
U.S. Appl. No. 12/514,311 Official Action (Advisory Action) dated Aug. 5, 2015 (6 pages).
European Application No. 10192477.7 Official Action dated Jul. 6, 2015 (5 pages).
European Application No. 11768544.6 Response to Official Action dated Dec. 2, 2014, submitted May 29, 2015 (12 pages).
U.S. Appl. No. 13/640,519 Response to Official Action (Final) dated Oct. 1, 2014, submitted Dec. 28, 2014 (15 pages).
U.S. Appl. No. 13/640,519 Official Action (Non-Final) dated May 6, 2015 (13 pages).
European Application No. 12734200.4 Response to Official Communication dated Sep. 4, 2014, submitted Mar. 4, 2015 (16 pages).
U.S. Appl. No. 13/978,538 Official Action (Non-Final) dated Jan. 23, 2015 (24 pages).
U.S. Appl. No. 13/978,538 Response to Official Action (Non-Final) dated Jan. 23, 2015, submitted May 21, 2015 (13 pages).
U.S. Appl. No. 13/978,538 Official Action (Non-Final) dated Jul. 24, 2015 (16 pages).
European Application No. 12805094.5 Supplementary Partial European Search Report dated Feb. 23, 2015 (8 pages).
European Application No. 12805094.5 Response to Supplementary Partial European Search Report submitted Apr. 2, 2015 (1 page).
European Application No. 12805094.5 Supplementary European Search Report dated Jun. 30, 2015 (14 pages).
U.S. Appl. No. 13/924,572 Response to Official Action (Non-Final) dated Dec. 2, 2014, submitted Mar. 26, 2015 (11 pages).
U.S. Appl. No. 13/924,572 Official Action (Non-Final) dated May 14, 2015 (12 pages).
PCT Appl. No. PCT/IB14/62106 International Search Report and Written Opinion dated Feb. 24, 2015 (8 pages).
PCT Appl. No. PCT/IB15/50873 International Search Report and Written Opinion dated Jun. 25, 2015 (8 pages).

\* cited by examiner

METHODS, APPARATUS AND SYSTEMS FOR OPERATING A MEDICAL DEVICE INCLUDING AN ACCELEROMETER

FIELD OF THE INVENTION

The present invention relates generally to the field of medical devices. More specifically, the present invention relates to methods, apparatus and systems for operating a medical device including an accelerometer.

BACKGROUND

Medical devices operate for therapeutic and/or diagnostic uses. Some exemplary medical devices may be: blood pressure monitors which may monitor a patient's blood pressure and heart rate, electrical thermometers which may measure a patient's body temperature and many more.

Some medical devices may administer fluid to a patient via a conduit such as a flexible tube. Some medical devices may monitor fluid flowing through its system and connected to one or more of a patient's bodily fluids. For example a peristaltic pumps which may be used to infuse medicines into a vein. In another example, a dialysis machine may pass a patient's blood through the machine to filter and get rid of toxins and excess fluids.

Some medical devices administering fluid or monitoring fluid may want to control the rate at which the fluid is flowing within the system. In some medical devices a flow rate may be achieved by carrying out preliminary tests on the medical device to correlate an expected flow rate to secondary features of the medical device such as motor rate and more.

A medical device may be used in a hospital, doctor or nurse's office or other medical treatment centers. Medical devices may also be used at patient's homes or personal environments.

SUMMARY OF THE INVENTION

The present invention includes a medical device, including a therapeutic component which may provide therapeutic functionality whilst in a therapeutic mode and may enter a device sleep mode (DSM). The medical device may include an accelerometer which may identify a movement characterization of the therapeutic component and a movement analysis module (MAM) which may receive the movement characterization from the accelerometer and determine a malfunction parameter. The MAM may be operable while the therapeutic component is in said DSM.

According to some embodiments, the medical device may include an output and a MAM controller. The MAM controller may be configured to receive a malfunction parameter and cause a warning to be displayed on said output if the malfunction parameter is above a predefined threshold.

According to some embodiments, the medical device may include an event logger module to store movement characterization.

According to some embodiments, the event logger module may be configured to relay movement data when said therapeutic component transitions to an awake mode. The event logger module may configured to store a malfunction parameter, and may relay the malfunction parameter when the therapeutic component transitions to an awake mode.

According to some embodiments, movement characterization may be selected from the group consisting of: acceleration data, vibration data, 1D acceleration data, 2D acceleration data, 3D acceleration data. 1D vibration, 2D vibration and 3D vibration. Movement characterization may include one or more of the following information content: acceleration data, acceleration profile, time interval, acceleration axis; event time and date; vibration time interval and sequence of vibration.

According to some embodiments, the medical device may include a beacon module configured to emit a beacon based on a detected malfunction parameter received from the MAM. The beacon may include at least one of the signals selected from: an audible alarm, a visual alarm, a wireless radio signal and a notification.

According to some embodiments, the MAM may be further configured to detect a suspected theft based on movement characterization and trigger a beacon.

According to some embodiments, the device sleep mode may be selected from the group consisting of: a deep sleep mode and a sleep mode.

According to some embodiments, the therapeutic component may have a normal mode and the MAM may be configured to cause the therapeutic component to automatically transition between said device sleep mode and said normal mode.

According to some embodiments, a medical device, may include a therapeutic component adapted to provide therapeutic functionality having an operative mode, an accelerometer configured to identify a movement characterization of the therapeutic component; a movement analysis module (MAM) configured to receive the movement characterization from the accelerometer and determine a malfunction parameter and an alarming module configured to trigger an alarm if a malfunction parameter is determined during operative mode.

According to some embodiments, movement characterization may be a change in orientation above a predefined orientation threshold above which operation of the therapeutic component may be considered dangerous for use. The malfunction parameter may be configured to cause deactivation of said therapeutic component.

According to some embodiments, a medical device may include a therapeutic component adapted to provide therapeutic functionality, an accelerometer configured to identify a movement characterization of the therapeutic component, a movement analysis module (MAM) configured to receive the movement characterization from the accelerometer and determine a malfunction parameter; and a therapeutic controller configured to receive the malfunction parameter and based on said received malfunction parameter cause the therapeutic component to carry out at least one of the actions from the list consisting of: disable the therapeutic component, enable initiation of the therapeutic component and emit a warning regarding safety of using the therapeutic component.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
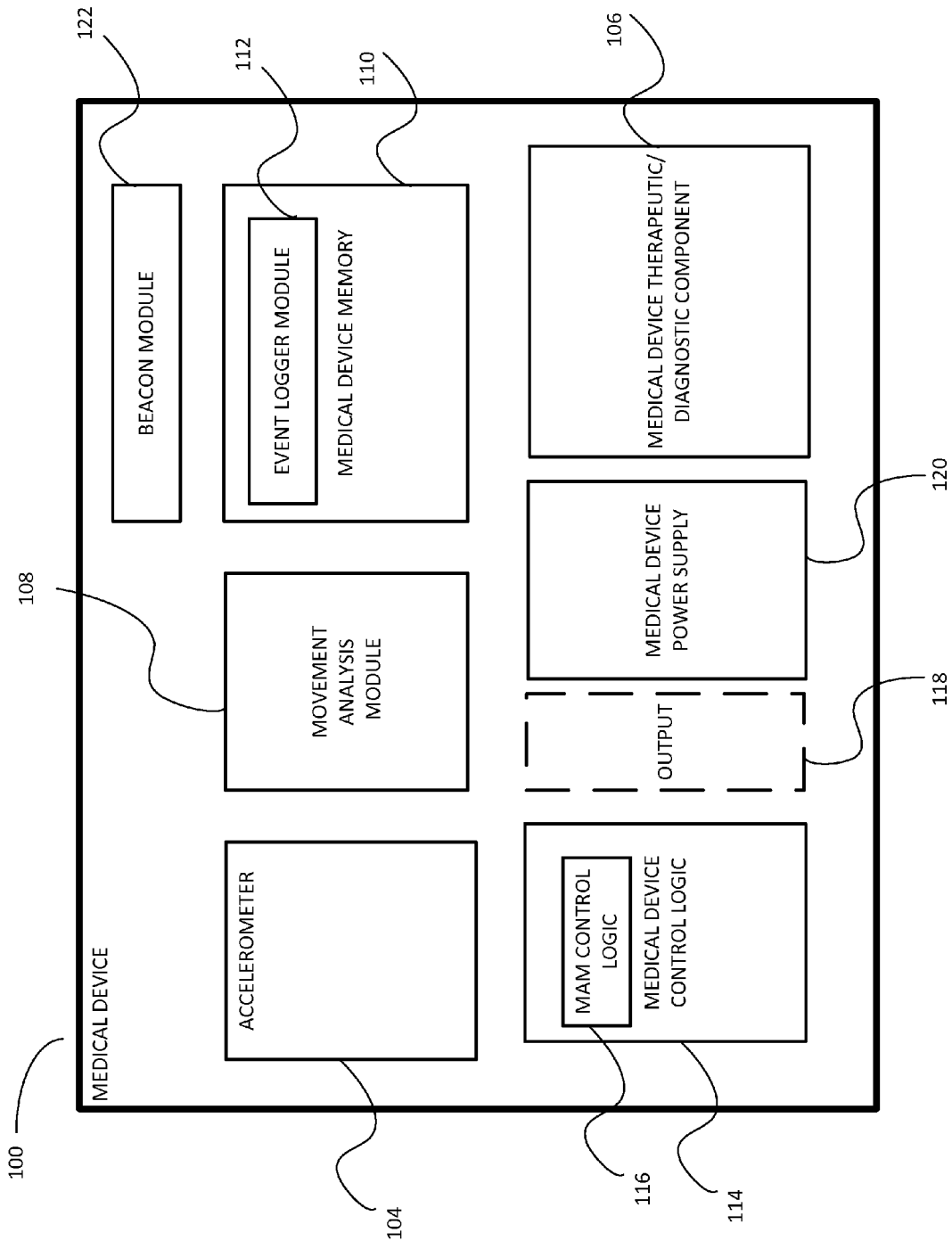
FIG. 1 is a functional block diagram of an exemplary medical device according to embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

Unless specifically stated otherwise, as apparent from the following discussions, it is appreciated that throughout the specification discussions utilizing terms such as "processing", "computing", "calculating", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

A medical device may be used in a hospital, doctor or nurse's office or other medical treatment centers or in patient's homes or personal environments and more. Medical devices may fall or be susceptible to use that may render the medical device inoperable or dangerous for use. Detection of such occurrences may be very relevant when the medical is not in use for example, in storage or in transition as well as during regular medical operation of the medical device. Accordingly, a medical device including an accelerometer is described including a power save mode so that critical occurrences may be detected and a user may be notified of such occurrences even if they occurred while the medical device was not in operation. Additional operations and functionalities such as theft detection and in-use movement detection are also described.

Turning now to FIG. 1, depicted is a functional block diagram of an exemplary medical device, such as medical device 100, according to embodiments of the present invention. Medical device 100 may include one or more accelerometers such as accelerometer 104. Accelerometer 104 may be configured to measure or detect acceleration of a device. The acceleration measured by accelerometer 104 may be defined as a movement characterization and may be the coordinate acceleration (rate of change of velocity) and/or the g-force acceleration of medical device 100 or otherwise. According to some embodiments, single-axis and multi-axis models of accelerometer 104 may be configured to detect magnitude and direction of the acceleration, as a vector quantity or parameter, and can be used to sense orientation, coordinate acceleration, vibration, shock, falling and more. Medical device 100 may include a medical device therapeutic/diagnostic component such as therapeutic/diagnostic component 106. Therapeutic/diagnostic component 106 may be a peristaltic pump, dialysis machine, heart-lung machine and more. Therapeutic component 106 may have a therapeutic functionality such as delivering a medical drug intravenously, administering fluid to a patient, carrying out dialysis on a patient and more.

Accelerometer 104 may be a standalone or off-the shelf element of medical device 100 or may be embedded within one or more blocks or elements of medical device 100 described below.

Medical device 100 may include a movement analysis module (MAM) such as MAM 108. MAM 108 which may be configured to detect or determine acceleration, vibration, movement, theft, orientation and more of medical device 100 based on input received directly or indirectly from accelerometer 104 and/or additional information.

According to some embodiments, medical device 100 may include a memory such as medical device memory 110 which may further include an event logger module such as event logger module 112. Medical device memory 110 may include one or more types of memory storages such as RAM, ROM, DRAM, hard drive, flash memory and or a combination of memory types.

According to some embodiments, accelerometer 104 may relay information and/or data detected by the accelerometer 104 directly to MAM 108, event logger module 112 and/or medical device memory 110. The information relayed may be in parameter and/or vector format.

According to some embodiments, MAM 108 may receive information directly from accelerometer 104, medical device memory 110 and/or event logger module 112. MAM 108 may receive all data, all data within a predetermined time/date interval, last predefined interval of events, all events above a threshold, all events determined by an axis filter, all events determined by an interval filter or otherwise.

According to some embodiments, MAM 108 may calculate the probability of a malfunction and output or determine a malfunction parameter. For example, MAM 108 may receive information associated with accelerometer data such as acceleration events, vibration events and more, and calculate or determine a malfunction parameter such as: calculate three dimensional position of medical device 100, determine if medical device 100 was exposed to hazardous acceleration, determine if medical device 100 was exposed to hazardous impact forces, determine if medical device 100 was exposed to hazardous vibrations and more. MAM 108 may take into account the amount, length and intensity of the exposures and more.

According to some embodiments, MAM 108 malfunction parameter(s) may be stored in event logger module 112, medical device memory 110, internally in MAM 108 or otherwise.

According to some embodiments, medical device 100 may include a control logic such as medical device control logic 114 which may further include a dedicated section for controlling MAM 108 or to receive controls from MAM 108, such as MAM control logic 116. Medical device control logic 114 may control and receive information from additional blocks such as therapeutic/diagnostic component 106, medical device memory 110, accelerometer 104 and more.

According to some embodiments, malfunction parameter(s) calculate/determined at MAM 108 may cause many different safety actions in medical device 100. Several examples, some of which may occur concurrently are: continuous work of the medical device may be enabled, medical device 100 or therapeutic/diagnostic component 106 may be disabled, a beacon may be caused to be emitted, acceleration events and/or vibration events as well as malfunction parameter(s) may be sent to medical device memory 110 to be stored and/or accessed by an external user (such as a technician), acceleration events and/or vibration events as well as malfunction parameter(s) may be sent to medical device memory 110 to be stored and/or to a remote server in order to be used for statistical analysis of malfunctions and their results.

Some examples of events and safety actions follow. An extremely hazardous event may be detected by MAM 108 which may disable therapeutic/diagnostic component 106 until a technician or authorized personnel input a code that medical device 100 has been tested and is authorized to be used again. A first type of hazardous event may cause medical device 100 to emit a warning, for example, that it is not advised to use medical device 100. A second type of hazardous event may cause a recommendation that medical device 100 not be used until calibration is confirmed. A third type of hazardous event may cause a list of recommended maintenance and/or calibration procedures to be issued. Ongoing recommendations of how to better protect maintain medical device 100 may be issued based on recurring or statistical hazardous events occurring.

According to some embodiments, accelerometer data, acceleration events, vibration events may include: acceleration profile, acceleration time interval, vibration length, vibration interval, vibration length, vibration time interval, acceleration axis, event time, and date. Optionally, vibration events and acceleration events may include information regarding direction of the events on one, two or three dimensional axis.

According to some embodiments, medical device 100 may include an output such as output 118. Output 118 may be internal or external to medical device 100. Output 118 may be a screen such as a touch screen, LCD screen, color screen a display, an audio display and more. In some embodiments, such as a touch screen, output 118 is also an input. Data and/or information detected by the accelerometer may be used so that the display on output 118 is displayed upright. Output 118 may further display information relating to acceleration events, vibration events, malfunction parameters and more.

According to some embodiments medical device 100 may include a power supply such as medical device power supply 120. Medical device control logic 114 and/or MAM control logic 116 may be configured to activate and de-activate different elements of medical device 100 such as: accelerometer 104, MAM 108 event logger module 112 and more so that low power consumption activation of medical device 100 is achieved.

For example, accelerometer 104 may operate or be operative in a "deep sleep" mode of medical device 100. In this mode, while therapeutic/diagnostic component 106, MAM 108 and medical device memory 110 including event logger module 112 are in standby mode or turned off or deactivated accelerometer 104 may still detect movement characterization thus conserving energy of medical device power supply 120. In this example if the accelerometer detects an extreme event (such as an event above a predefined threshold) then medical device control logic may awaken different elements of medical device 100 depending on the detected event. In one example, if a fall of medical device 100 is detected then event logger module 112 may be turned on temporarily to store the event or the whole medical device 100 may be turned on to emit a signal to an external server to store the event.

In another example, accelerometer 104 may operate in a "sleep" mode. In this mode: while therapeutic/diagnostic component 106 are in standby mode or turned off thus conserving energy of medical device power supply 120, MAM 108 and/or event logger module 112 continuously and/or periodically turn on to store acceleration events or information received from accelerometer 104. In this example when medical device 100 awakens or is activated to start a therapeutic/diagnostic functionality if a hazardous event is stored in event logger module 112 then a warning is emitted and may be displayed on output 118 as described in this application.

In another example, accelerometer 104 may operate in a "normal" mode. In this mode: MAM 108 continuously receives input directly or indirectly from accelerometer 104.

According to some embodiments, medical device 100 may switch between some or all of the aforementioned modes and additional modes: deep sleep mode, sleep mode and normal mode automatically. For example, if medical device power supply 120 is detected to be a substantially constant supply such as a power outlet then medical device 100 may switch to sleep mode or normal mode depending on additional inputs/information. In another example, medical device 100 may switch from deep sleep mode to sleep mode if many substantial events are detected. In another example, medical device 100 may switch to normal mode if an extreme event is detected. A device sleep mode (DSM) may also include a deep sleep mode and a sleep mode and/or transition between the two. It is further understood that while medical device 100 is in a sleep mode, DSM or deep sleep mode only some of the blocks may be deactivated while some of the blocks are at least partially operable. For example, therapeutic component 106 may be turned off/deactivated while accelerometer 104 is still operable and may still detect a movement characterization of medical device 100. Additional or transitional modes and/or sub-modes depending on system configurations and operability of medical device 100 are understood.

According to some embodiments, event logger module 112 may receive information and data from movement analysis module 108, accelerometer 104 and/or additional blocks and modules of medical device 100 such as a clock, timer, counter and more. Event logger module may store data such as: acceleration events, vibration events, malfunction parameters and more. The data stored in event logger module 112 may be stored as parameters, or as vectors such as 1 dimensional (1D), 2 dimensional (2D), 3 dimensional (3D) and more and may tie different elements of data to each other. For example, 1D vector may be used to store acceleration data in one direction while 2D may be used to store acceleration in 2 different axis's Event logger module 112 may store data or information selectively and/or efficiently, for example, may only store events above a predefined threshold.

According to some embodiments, data stored in event logger module 112 may be output upon request and/or periodically. How and when data is output from event logger module 112 may also be dependent on the request received and/or the mode of operation that medical device 100 is operating in (normal mode, sleep mode and so on). Event logger module 112 may further receive a command/instructions to delete some/all data for example after it has been output or after medical device 100 has been calibrated or otherwise.

According to some embodiments, medical device 100 may include a beacon device such as beacon module 122. Beacon module 122 may be configured so that, dependent on a received instruction or signal, a beacon is emitted. A beacon may include: an audible alarm, a visual alarm, a signal (such as a wireless signal, Wi-Fi, Bluetooth or otherwise) or a notification (textual or otherwise) on output 118. Accordingly, beacon module 122 may include a speaker, LEDs, lights, one or more antenna and/or outputs to various additional elements of medical device 100. Beacon module 122 may also be considered or referred to as an alarming module.

Figure 2:
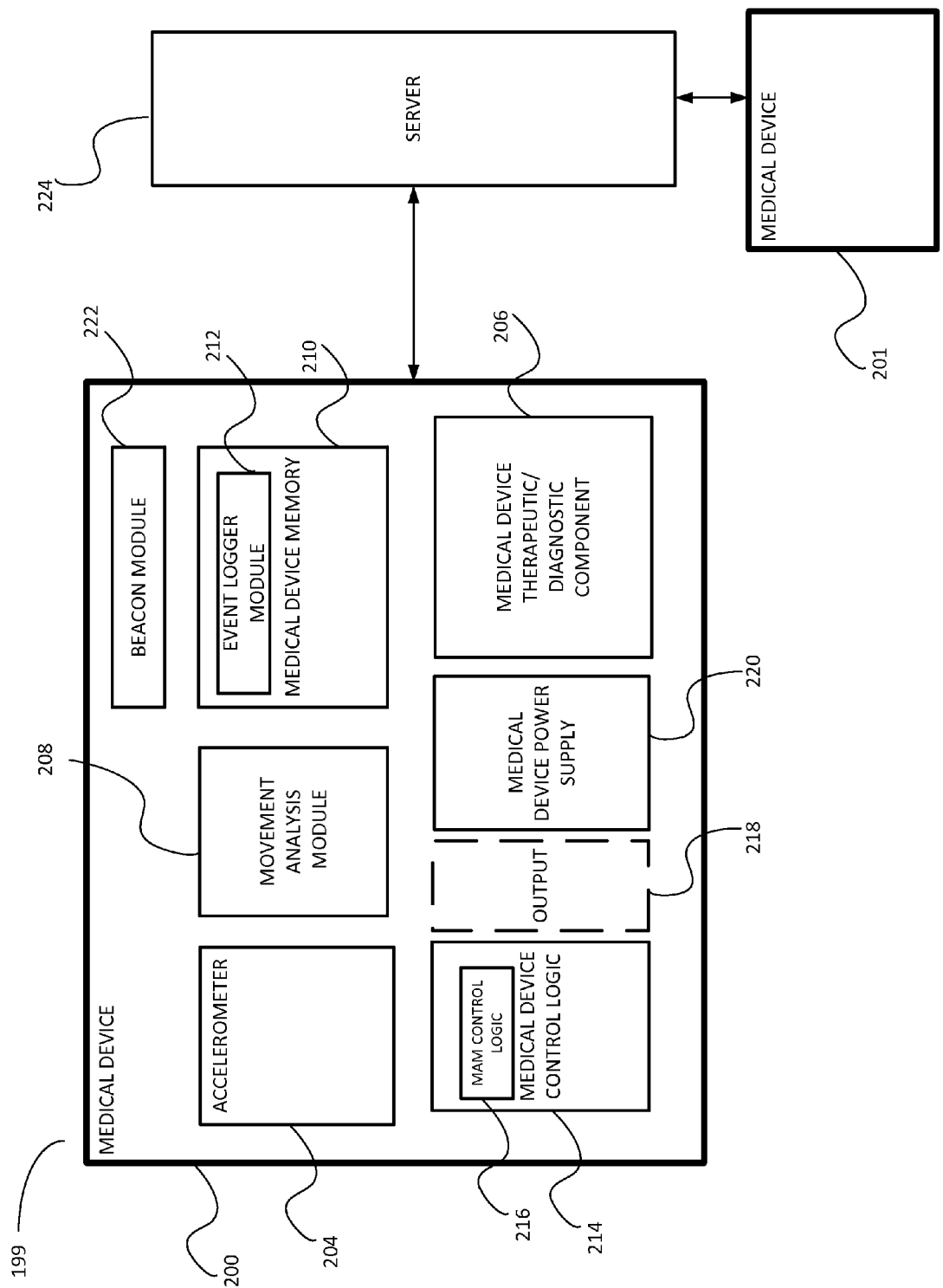
FIG. 2 is a functional block diagram of an exemplary medical device arrangement according to embodiments of the present invention.

Turning now to FIG. 2, depicted is a medical device arrangement (199), including at least one medical device such as medical device 200 and a remote server such as server 224 according to some embodiments of the present invention. Optionally, arrangement 199 may include additional medical devices such as medical device 201 which may be similar or different than medical device 200 and/or additional servers which may be similar or different than server 224. It is understood that medical device 200 is substantially similar to medical device 100 described above and accordingly elements 204-222 are substantially similar to elements 104-122 (accordingly).

According to some embodiments, medical device 200 may relay to server 224 acceleration events, vibration events and/or malfunction parameters and more. Server 224 may receive additional information from a technician or additional source (such as a database or a self-test carried out by medical device 200) including information indicating the outcome of one or more malfunction parameters. For example, movement analysis module 208 may warn that a specific acceleration event may have caused medical device 200 housing to have broken. A technician, checking medical device 200 may insert outcome information such as has the housing indeed been broken or not and the correlation between the malfunction parameter and the outcome may also be stored. Server 224 may use data such as acceleration events, vibration events, malfunction parameters and outcomes received from one or more medical devices to update the algorithms and to receive or calculate more information regarding malfunction parameters and the medical devices. A few examples: Server 224 may: (1) update dependency between acceleration events and/or vibration events and malfunction parameters, (2) calculate housing failures per acceleration/vibration events, (3) determine damage to medical device per acceleration/vibration events, (4) determine relationship between medical device therapeutic/diagnostic component characteristics (such as flow rate accuracy, force sensor accuracy and more) in correlation to acceleration/vibration events and (5) aid in investigation of recalls or near recalls.

According to some embodiments, server 224 may relay updates to medical device 200 including new algorithms for determining or calculating malfunction parameters.

Figure 3:
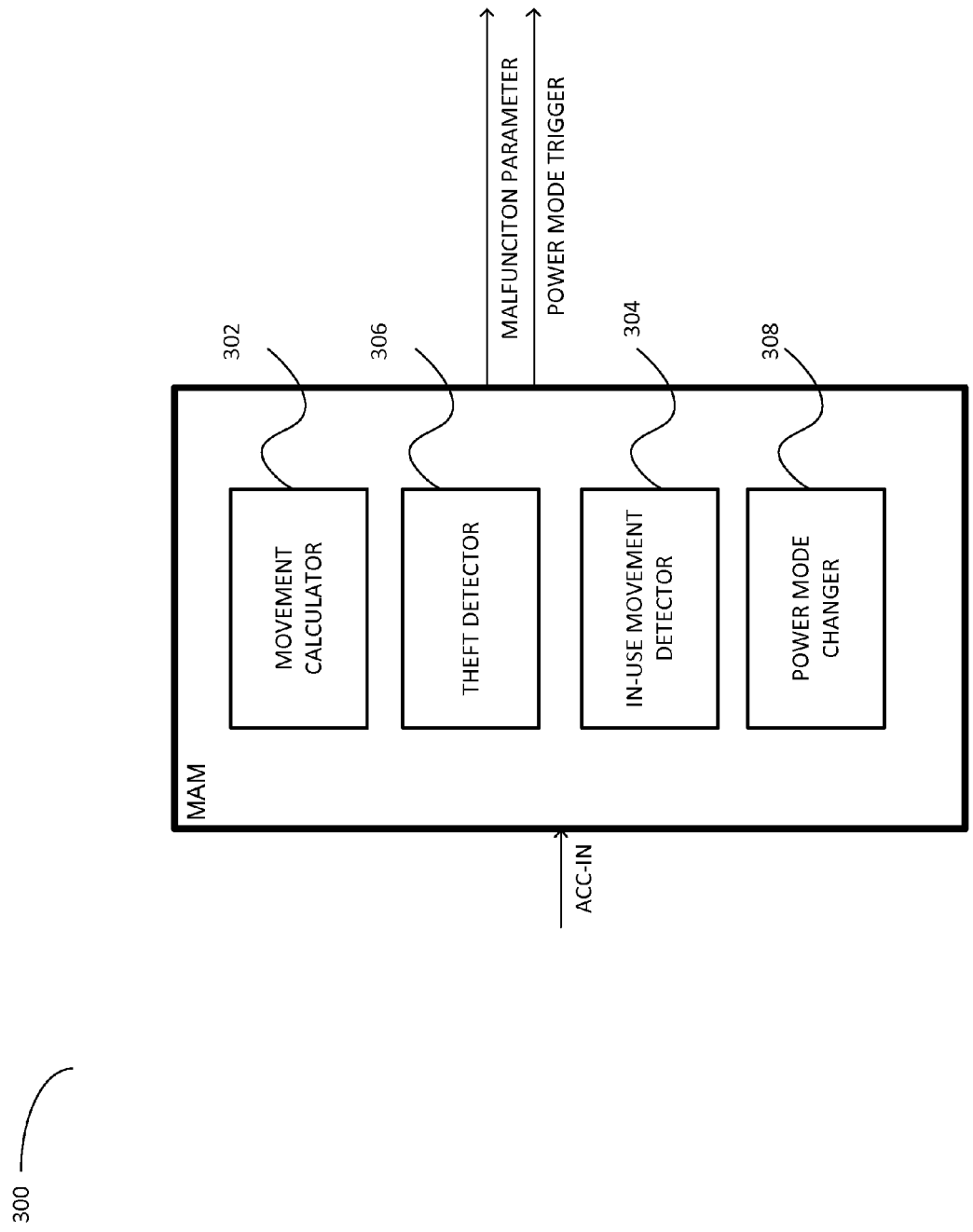
FIG. 3 is a functional block diagram of an exemplary Movement Analysis Module according to embodiments of the present invention.

Turning to FIG. 3, depicted is a functional block diagram of an exemplary Movement Analysis Module such as MAM 300 according to embodiments of the present invention. It is understood that MAM 300 is substantially similar to MAM 108 and 208 of FIG. 1 and FIG. 2 (respectively). Some functionality of MAM 300 has been described above with relation to FIG. 1 and FIG. 2, these and additional features, functionalities and characteristics of MAM 300 will now be further discussed.

MAM 300 may receive one or more inputs (depicted as ACC-in in FIG. 3) which may include acceleration events and/or vibration events and more and output a malfunction parameter. MAM 300 may include a calculator such as movement calculator 302 to determine a malfunction parameter based on received acceleration events/data, vibration events/data and more. MAM 300 may include an active movement detector, such as in-use movement detector 304, which may detect incorrect or dangerous movement of an associated medical device while the medical device is in use. In-use movement detector 304 may detect a malfunction parameter indicating a substantial change in a parameter of an associated medical device's position that may be hazardous while the associated medical device is in operation or administering a therapeutic or diagnostic action. A changed in a parameter of a position may be: a change in orientation, height, direction or otherwise. Based on the detected malfunction parameter MAM 300 may cause or trigger an associated medical device to: disable or lock the medical device, cause a beacon to be emitted, display a notification on an output of the associated medical device or enable continued use of the associated medical device a combination of these actions and more. The associated medical device may be enabled for continued use if the detected change in the associated medical device's position parameter is not substantial or no change is detected, or if for a specific scenario (specific treatment or diagnostic operation of the associated medical device) the detected change is not hazardous or otherwise.

For example, if an associated medical device is a peristaltic pump used to administer medical drugs to a patient some medical drugs may require that the peristaltic pump remain in an upright position to enable correct administration of the drugs. Accordingly in-use movement detector 304 may receive acceleration/vibration events as well as information regarding the medical treatment being administered and unsafe movements of the peristaltic during operation in-use movement. Based on these received input in-use movement detector 304 may detect a malfunction parameter indicating that the associated peristaltic pump has moved in a dangerous manner during administration of the medical drug and cause a warning alarm or cause the peristaltic pump to stop administering the drug. In another example, if an associated medical device is a dialysis machine in-use movement detector may detect if the dialysis machine has moved to a lower height which may be dangerous and trigger an alarm or cause the dialysis machine to stop pumping. Additional examples and combinations are understood.

According to some embodiments, MAM 300 may include a theft detecting module or circuit such as theft detector 306. Theft detector 306 may receive acceleration/vibration events, as well as additional information such as expected location of pump, authorized area for pump, actual location of pump and more, and calculate or determine a malfunction parameter which may indicate that suspicious or un-authorized movement of the medical device is taking place and/or that a theft is suspected.

According to some embodiments, authorized and actual location of a medical device associated with MAM 300 may be calculated/received based on predetermined grid of locations utilizing Wi-Fi or other wireless configurations or other known methods of mapping a predefined area.

According to some embodiments, based on the detected malfunction parameter indicating un-authorized movement, MAM 300 may cause or trigger an associated medical device to: disable or lock the medical device, cause a beacon to be emitted, display a notification on an output of the associated medical device or a combination of these actions and more.

According to some embodiments, MAM 300 may include power mode circuitry including power mode changer 308 configured to emit a power mode trigger signal to cause an associated medical device to transition between power modes. Transition between power modes may include activating and de-activate different elements of the associated medical device so that low power consumption activation is achieved as well as a safe operation of the associated medical device depending on the detected malfunction parameter. Some example of power modes are: "deep sleep" mode, "sleep" mode, standby mode and normal mode and more. Optionally, MAM 300 may receive additional inputs indicating source of the power supply, power levels, mode of operation (is medical device active in supplying medical treatment) and more and use these inputs to determine if a change in power mode is required. Optionally MAM 300, may output the power mode trigger based on limited received and detected signals and the associated medical device may utilize additional information (such as the aforementioned inputs indicating source of the power supply, power levels, mode of operation and more) and determine if a change in power mode will be carried out.

Figure 4:
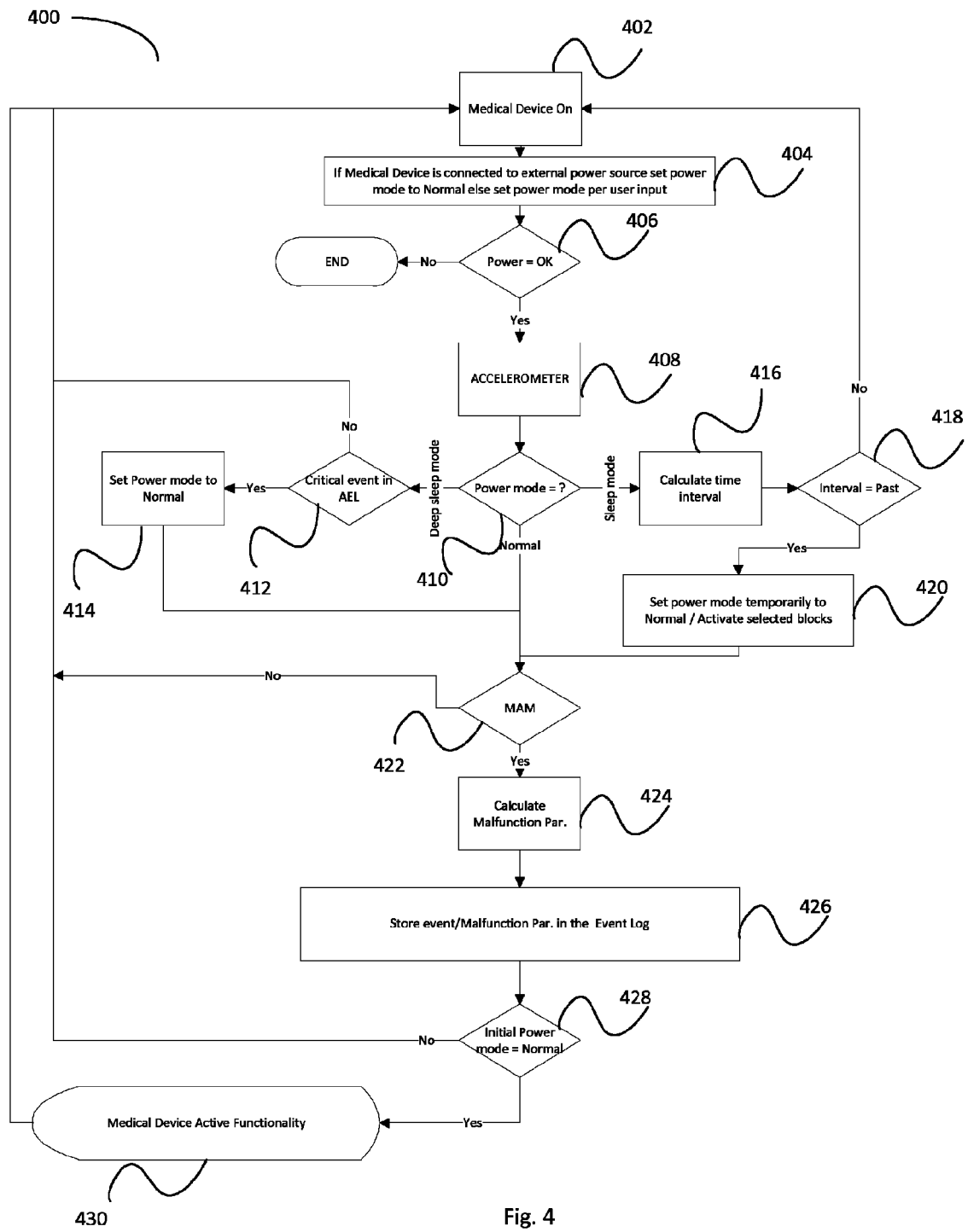
FIG. 4 is an example flow chart depicting a method of operating a medical device according to embodiments of the present invention.

Turning now to FIG. 4, shown is an example flow chart (400) of a method of operating a medical device according to embodiments of the present invention. A medical device is turned on either by a user or automatically—for example, periodically (step 402). If the medical device is connected to an external power source such as a power supply or an electrical grid or otherwise the medical device power mode is set to normal, otherwise the power mode may be determined by other parameters such as user input, default settings and/or level of power detected (step 404). If the level of power is identified as sufficient (step 406) the accelerometer is turned on to measure or detect acceleration/movement of the medical device (step 408). Depending on the power mode (step 410), the medical device may proceed to different actions or await detection by the accelerometer in order to proceed. For example, if in a deep sleep mode, the medical device may await detection of a critical event (step 412), after which the medical device may transition to normal mode (414). In another example, if the medical device is in a sleep mode the medical device may periodically (step 416 and step 418) transition to normal mode and/or activate selected blocks of the medical device (step 420). When in normal mode or in a partially active mode the Movement Analysis Model may be active (step 422) and calculate a malfunction parameter (424). During normal mode or partially active mode the malfunction parameter and/or acceleration events may be store in a medical device event logger module (step 426) and Movement Analysis module may also determine a power mode trigger to cause the medical device to transition to a different power mode. If the medical device was initially in normal mode (step 428), and did not transition to normal mode temporarily due to a critical event or otherwise (for example see step 414 and step 420) the medical device may continue to its awake mode or active functionality for example, carrying out a therapeutic or diagnostic functionality (step 430). It is understood, that during the example method of operation described above, if a step is not determined as positive or "yes" then the method may transition to step 402 or a different step. Additional algorithms in accordance with additional block descriptions described above are understood.

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

What is claimed:

1. A medical device, comprising:
a power source;
a therapeutic assembly including electric circuits and at least one electromechanical component, wherein said assembly is adapted to use electricity from said power source to introduce a therapeutic substance into a body of a person whilst operating in a therapeutic mode, and is further adapted to enter a device sleep mode (DSM) during which mode said assembly is not introducing a therapeutic substance into a body of a person;
an accelerometer circuit mechanically linked to said therapeutic assembly and configured to, when the therapeutic assembly is in DSM, sense movements of said therapeutic assembly and to generate movement characterization data indicative of at least one sensed movement of said therapeutic assembly; and
a movement analysis module (MAM) configured to, during DSM, receive the movement characterization data from the accelerometer and to estimate whether a sensed movement of said therapeutic assembly represents a malfunction parameter requiring testing or recalibration of said assembly before a next use of said device, and triggering a disabling of said therapeutic assembly upon estimating a malfunction parameter.

2. The medical device according to claim 1, further comprising an output and a MAM controller, wherein said MAM controller is configured to, upon detection of a malfunction parameter, cause a warning to be displayed on said output.

3. The medical device according to claim 1, further comprising an event logger module to store movement characterization data.

4. The medical device according to claim 3, wherein said event logger module is configured to relay said movement characterization data when said therapeutic assembly transitions to an awake mode.

5. The medical device according to claim 1, wherein said event logger module is configured to store a malfunction parameter.

6. The medical device according to claim 5, wherein said event logger module is configured to relay said malfunction parameter when said therapeutic assembly transitions to an awake mode.

7. The medical device according to claim 1, wherein movement characterization data includes one or more movement characterizations selected from the group consisting of: acceleration, vibration, 1D acceleration, 2D acceleration, 3D acceleration, 1D vibration, 2D vibration and 3D vibration.

8. The medical device according to claim 7, wherein movement characterization data further comprises one or more of the following movement characterizations: acceleration data, acceleration profile, time interval, acceleration axis; event time and date; vibration time interval and sequence of vibration.

9. The medical device according to claim 1, further comprising a beacon module configured to emit a beacon based on a detected malfunction parameter received from the MAM.

10. The medical device of claim 9, wherein the beacon is at least one of the signals selected from: an audible alarm, a visual alarm, a wireless radio signal and a notification.

11. The medical device according to claim 9, wherein said MAM is further configured to detect a suspected theft based on movement characterization data and trigger a beacon.

12. The medical device according to claim 1, wherein said device sleep mode is selected from the group consisting of: a deep sleep mode and a sleep mode.

13. The medical device according to claim 12 wherein said therapeutic assembly has a normal mode and said MAM is configured to cause said therapeutic assembly to automatically transition between said device sleep mode and said normal mode.

14. A medical device, comprising:
- a therapeutic assembly comprising electromechanical components adapted to introduce a therapeutic substance into the body of a person;
- an accelerometer adapted to sense movement and orientation of the therapeutic assembly;
- a movement analysis module (MAM) comprising processing circuits configured to receive signals from said accelerometer indicating movement and orientation of the therapeutic assembly sensed by said accelerometer;
- and to trigger an alarm circuit if the signals received from said accelerometer match values indicating a malfunction;
- and triggering a disabling of said therapeutic assembly upon estimating a malfunction parameter.

15. The medical device according to claim 14, wherein signals indicating a change in orientation above a predefined orientation threshold above which operation of said therapeutic component is considered dangerous for use triggers an alarm circuit and triggering a disabling of said therapeutic assembly upon estimating a malfunction parameter.

* * * * *